United States Patent [19]

Weitkamp et al.

[11] Patent Number: 4,795,847

[45] Date of Patent: Jan. 3, 1989

[54] PREPARATION OF 2,6-DIALKYL-NAPHTHALENES

[75] Inventors: Jens Weitkamp, Oldenburg; Marita Neuber, Karlsruhe; Wilhelm Höltmann, Munster; Gerd Collin, Duisburg; Hans Spengler, Olfen, all of Fed. Rep. of Germany

[73] Assignee: Rutgerswerke Aktiengesellschaft, Fed. Rep. of Germany

[21] Appl. No.: 151,697

[22] Filed: Feb. 2, 1988

[30] Foreign Application Priority Data

Feb. 4, 1987 [DE] Fed. Rep. of Germany ....... 3703291

[51] Int. Cl.$^4$ .............................................. C07C 2/68
[52] U.S. Cl. ....................................... 585/467; 502/60
[58] Field of Search ......................... 585/467; 502/62

[56] References Cited

U.S. PATENT DOCUMENTS

| | | | |
|---|---|---|---|
| 3,525,775 | 8/1970 | Bolton et al. | 502/62 |
| 4,375,573 | 3/1983 | Young | 585/475 |
| 4,482,774 | 11/1984 | Koetsier | 585/467 |
| 4,508,836 | 4/1985 | Haag et al. | 585/466 |

FOREIGN PATENT DOCUMENTS

| | | | |
|---|---|---|---|
| 0012514 | 6/1980 | European Pat. Off. | 585/467 |
| 0202752 | 11/1986 | European Pat. Off. | 585/467 |
| 1036232 | 2/1986 | Japan | 585/467 |

*Primary Examiner*—Patrick P. Garvin
*Assistant Examiner*—Elizabeth Irzinski
*Attorney, Agent, or Firm*—Bierman and Muserlian

[57] ABSTRACT

A process for the preparation of 2,6-dialkyl-naphthalenes comprising selectively alkylating naphthalene or 2-alkyl-naphthalene with alkylating agent in the presence of a zeolite catalyst at 250° to 345° C. which dialkyl-naphthalenes are useful for the preparation of naphthalene 2,6-dicarboxylic acid used to produce high-quality polyesters or polyamides.

8 Claims, No Drawings

PREPARATION OF 2,6-DIALKYL-NAPHTHALENES

STATE OF THE ART

DE-A No. 3,334,084 describes a process for methylation of naphthalene or 2-methyl-naphthalene with methanol or dimethyl ether on a zeolite catalyst of the pentasil type, preferably ZSM-5 at temperatures of 350° to 600° C., preferably 400° to 550° C. According to the data in the examples, the conversion of naphthalene by reaction with methanol to 2-methyl-naphthalene had good yields and high selectivity. The examples show the reaction of 2-methyl-naphthalene with methanol gave good yields and high selectivity in the formation of 2,6-dimethyl-naphthalene as the main product but with considerable amounts of 1-methyl-naphthalene. Attempts to reproduce the method showed disadvantages and particularly, it was found that the quantitative values for 2,6-dimethyl-naphthalene also included 2,7-dimethyl-naphthalene which isomers can hardly be separated by conventional gas chromatography. The two isomers were present in approximately equal amounts.

Chem. Ab., Vol. 104, 56695a describes a process for alkylation of naphthalene with a mixture of H$^+$-Zeolite and $\gamma$-aluminum oxide which resulted in a mixture of 2,6-dimethyl-naphthalene and 2,7-dimethyl-naphthalene at a molar ratio of 41.2% to 37.8%.

OBJECTS OF THE INVENTION

It is an object of the invention to provide a process for the preparation of 2,6-dialkyl-naphthalenes with high yield and selectivity and a long catalyst life.

This and other objects and advantages of the invention will become obvious from the following detailed description.

THE INVENTION

The novel process of the invention for the preparation of 2,6-dialkyl-naphthalenes comprises selectively alkylating naphthalene or 2-alkyl-naphthalene with alkylating agent in the presence of a zeolite catalyst at 250° to 345° C.

By effecting the alkylation reaction 5° to 100° C. lower than the prior art process, the alkylation activity of the catalyst decreases negligibly and a long catalyst life is obtained at a nearly constant conversion rate. Surprisingly, further greater cost-efficiency effects of the process were found in the reaction being more selective with decreasing reaction temperatures with a greater shift in the amount of 2,6-dialkyl-naphthalene produced.

For example, the ratio of 2,6-dimethyl-naphthalene to the total dimethyl-naphthalenes after 2 hours reaction time at 400° C. is 0.42 and after 2 hours at 300° C. is 0.52. When using 2-alkyl-naphthalene with decreasing reaction temperature, the rate of formation of 1-alkyl-naphthalene decreases more strongly than that of the alkylation products and the selectivity for the unwanted by-product 1-alkyl-naphthalene, thus, becomes less. The disturbing side reaction of the isomerization of 2-alkyl-naphthalene, i.e., the formation of 1-alkyl-naphthalene, occurs preferentially on the fresh catalyst.

In the course of the reaction, the catalyst centers, which catalyze the interfering isomerization, are clearly blocked and the conversion of 2-alkyl-naphthalene under these conditions then corresponds nearly to the formation of dimethyl-naphthalene. For example, the proportion of 1-methyl-naphthalene in the reaction mixture, which at the beginning of the conversion is approximately 4.5%, decreases relatively rapidly and amounts after 12 hours (340° C.) to less than 1%.

It has been found that this change of the transalkylation activity is brought about by the formation of carbon residue on the catalyst surface that occurs through carbonization of parts of the used reaction partners on the catalyst. It was furthermore found that this transalkylation can largely be avoided so that formation of 1-alkyl-naphthalene can be decreased to below 0.1% if for the alkylation reaction an already precarbonized zeolite can be used as catalyst, that is, a zeolite over which a gaseous organic material can be guided at temperatures around its decomposition point with carbon being deposited on the surface of the zeolite. Any vaporizable organic compound can be used as reagents for the carbonization. To avoid the generation of components which potentially interfere with or contaminate the planned conversion, alcohols, olefins, or alkyl-naphthalenes should be considered as reagents for the carbonization particularly, those which function as reactants in the subsequent conversion.

This pre-carbonization of the catalyst can take place in the temperature range of 250° to 600° C., preferentially between 300° to 450° C. To ensure that a sufficient quantity of carbon can form on the catalyst and/or in its pores to suppress isomerization of 2-alkyl-naphthalene, enough of the reagents should be carbonized that between 1 and 8 grams of carbon are deposited per gram of dry catalyst. Carbonization of the catalysts is suitably carried out in the same reactor in which subsequently, the alkylation reaction takes place. The reagents can, in this connection, be added either as a liquid phase or can be evaporated in a part of the reactor and added in the gaseous state, possibly with an inert carrier gas. Immediately after the carbonization, the alkylation of 2-alkyl-naphthalene can be started.

The conversion is a function of the crystallite size of the zeolite used. For example, comparable zeolites with different crystallite size under the same conditions yield in the alkylation reaction of 2-methyl-naphthalene with methanol, the following conversions of 2-methyl-naphthalene:

Crystallite size and conversion of 2-methyl-naphthalene (%) on HZSM-5 at 340° C.:

| Reaction time (h) | 0.25 | 1 | 2 | 5 | 10 |
| --- | --- | --- | --- | --- | --- |
| 1 µm | 20 | 17.5 | 15.5 | 13 | 11 |
| 2 µm | 11.5 | 9.5 | 8.3 | 7 | 6 |
| 16 µm | 6.5 | 5.5 | 4.7 | 4 | 3.5 |

The crystallite size, i.e., the average diameter of the zeolite crystallite, can be in the range of 0.091 to 20 µm and preferred is a range of 0.05 to 2 µm, which can be achieved with tolerable expenditures, on the one hand, and on the other hand, yields good conversion at low temperatures. Carrying out the conversion according to the invention takes place in a reactor known per se which is loaded with the zeolite catalyst and which is heated by a heater to the appropriate reaction temperature. The reagents are either added as liquid and evaporated in a part of the reactor or are supplied in the gaseous state, if necessary with a carrier gas, and guided over the catalyst. The contact time here is 0.1 to 0.5 seconds.

Examples of reagents are naphthalene or 2-alkyl-naphthalenes like 2-methyl-, 2-ethyl-2-propyl-, or 2-isopropyl-naphthalene on the one hand, and examples of alkylating agents are low molecular weight alcohols, dialkylether, or alkylhalides. Examples of such alkylating agents are methanol, dimethylether, methylbromide, ethanol, ethyl chloride, propanol or isopropanol.

Preferred reagents are 2-methyl-naphthalene and methanol or dimethylether. 2-methyl-naphthalene can be used either pure or as a mixture of 1- and 2-methyl-naphthalene. In addition, mixtures can be used as are generated in a preceding methylation reaction of naphthalene and contain, aside from 2-methyl-naphthalene as the main component, also 1-methyl-naphthalene and dimethyl-naphthalenes already. When using methyl-naphthalene mixtures as additional advantage of the method, a transalklylation is observed in the sense that more 2,6-dimethyl-naphthalene is formed than corresponds to the conversion of 2-methyl-naphthalene.

The molar ratio of methyl-naphthalene to methanol or dimethylether can vary in the wide range of 10:1 to 1:5 and the amount of dimethyl-naphthalenes formed in the presence of greater amounts of methanol or dimethylether is increased. On the other hand, at high proportions of methanol or dimethylether, increasingly higher methylated naphthalenes are formed and consequently, the preferred ratio is in the range of 1:1 to 1:05.

Catalysts for the alkylation reaction are zeolites of various kind, particularly those whose pores are formed of 10 or 12 oxygen atoms, so-called 10-ring or 12-ring zeolites. It has been found that the effective pore width of the zeolite is decisive for the selective alkylation of naphthalene and 2-alkyl-naphthalenes to 2,6-dialkyl-naphthalenes.

As a measure of the effective pore width of 12- and 10-ring zeolites, the "spaciousness index" (SI) is best used [Weitkamp et al, Appl. Catal., Vol. 27, p. 207–210 (1986)]. It can be determined simply in a catalytic test reaction in which a naphthalene with 10 carbon atoms, particularly butylcyclohexane or pentylcyclopentane, is converted on a bifunctional form (acidic and hydrogenation/dehydrogenation-active) of zeolite. The spaciousness index is then defined as the quotient of the selectivity for isobutane and n-butane ($SI = n_{i\text{-}butane}/n_{n\text{-}butane}$). In Table 1, the values of the spaciousness index for some zeolites are listed.

TABLE 1

| Spaciousness Indices of some zeolites | |
|---|---|
| Zeolite | SI |
| Y | 21 |
| ZSM-20 | 21 |
| Beta | 19 |
| L | 17 |
| Mordenite | 7 |
| EU-1 | 5 |
| Offretite | 5 |
| ZSM-12 | 3 |
| ZSM-5 | 1 |
| ZSM-22 | 1 |

The spaciousness index is a quantitative measure for the space available in a zeolite for catalytic conversion. The smaller the SI, the narrower are the pores and/or hollow spaces. It was found, that for the conversion of the invention, zeolites with a spaciousness index of 0.6 to approximately 12 can be used. For methylating or ethylating, zeolites with a spaciousness index of 0.6 to 5 are particularly suitable. For methylating naphthalene or 2-methyl-naphthalene, zeolites of type pentasil and especially ZSM-5 are particularly suitable. For alkylation reactions with bulky alkyl groups as, for example the isopropyl group, zeolites with a spaciousness index of 2 to 12 are preferred. The zeolites must be converted into a catalytically active form after synthesis and for that purpose, they are calcinated at temperatures of 300° to 700° C., preferably 400° to 600° C., to remove the organic template. To generate the active centers through ion exchange, $H^+$ or $NH_4^+$, metal ions like $Mg^{2+}$ or $Ca^{2+}$ particularly, three-valent metal cations like $Ce^{3+}$, $La^{3+}$ for example, or cations of the lanthanides or other multi-valent metal cations are introduced. By drying the exchanged zeolites at 250° to 600° C., preferably at 300° to 400° C., acid centers are generated. The Si/Al atom ratio of the zeolites can vary in a wide range of approximately 3 to >1000, preferred are Si/Al ratios between 15 and 200.

In the following examples there are described several preferred embodiments to illustrate the invention. However, it should be understood that the invention is not intended to be limited to the specific embodiments.

EXAMPLE

Description of the experimental apparatus

The experiments were carried out under atmospheric pressure in a fixed-bed flow apparatus. The reagents were added through a temperature-regulated saturator, through which nitrogen streams as the carrier gas. In a mixing vessel, both nitrogen streams were combined and then led into the reactor. For setting the streams, the reactor could be circumvented in a by-pass. The reactor is of quartz glass and streaming through the bulk catalyst on a frit was carried out from above. The reactor was heated by an electric oven and samples were taken on-line. Simultaneously, the reaction products were obtained by condensation in a condensation trap at 0° C. and the reaction products were analyzed by capillary gas chromatography.

Carrying out the experiments

The catalysts were compressed, ground and sifted and the grain fraction of 0.2 to 0.3 mm was used. The dry catalyst substance was 0.19 g and the zeolites were dried in situ in the nitrogen stream ($V_{N2} = 4.5$ l/h) at 500° C. for 6 hours.

Experimental conditions

| Catalyst | $NH_4ZSM\text{-}5$ |
|---|---|
| Reagents | 2-methyl-naphthalene (= 2-MN), $CH_3OH$ |
| Reaction temperature | 300° C. |
| Partial pressure of 2-MN | $P_{2\text{-}MN} = 0.019$ bar |
| Molar ratio | $n_{2\text{-}MN}: nCH_3OH = 1:0.5$ |
| Modified contact time | $W/F_{2\text{-}MN} = 160$ gh/mol |
| Catalyst substance, dry | $W = 0.19$ g |
| Contact time | $\tau = 0.2$ s |

Results

| Duration of reaction time | 0.5 h | 2 h | 8 h |
|---|---|---|---|
| Conversion (%) | 7 | 5 | 5 |
| Yields (%) | | | |
| naphthalene | <0.1 | <0.1 | <0.1 |
| 1-methyl-naphthalene | 1.5 | 0.5 | 0.5 |

-continued

| Duration of reaction time | 0.5 h | 2 h | 8 h |
| --- | --- | --- | --- |
| dimethyl-napthalenes | 5 | 4 | 4 |
| higher methylated naphthalenes | 0.5 | 0.5 | 0.5 |
| Composition of the dimethyl-naphthalene fraction (%) | | | |
| 2,6-dimethyl-naphthalene | 50 | 52 | 55 |
| 2,7-dimethyl-naphthalene | 34 | 33 | 32 |
| 1,3-+1,7-dimethyl-naphthalene | 4 | 3 | 2 |
| 1,6-dimethyl-naphthalene | 4 | 3 | 2 |
| 1,4-+2,3-dimethyl-naphthalene | 6 | 7 | 7 |
| 1,5-dimethyl-naphthalene | <0.01 | <0.01 | <0.01 |
| 1,2-dimethyl-naphthalene | 2 | 2 | 2 |

Various modifications of the process of the invention may be made without departing from the spirit or scope thereof and it is to be understood that the invention is intended to be limited only as defined in the appended claims.

What we claim is:

1. A process for the preparation of 2,6-dialkyl-naphthalenes comprising selectively alkylating naphthalene or 2-alkyl-naphthalene with a lower alcohol, dialkyl ether or alkyl halide as alkylating agent in the presence of a zeolite catalyst at 300° to 320° C.
2. The process of claim 1 wherein the alkylating agent is a methylating agent.
3. The process of claim 2 wherein 2-methyl-naphthalene is reacted.
4. The process of claim 1 wherein mixtures of methyl-naphthalenes are reacted.
5. The process of claim 1 wherein the zeolite has a spaciousness index of 1 to 12.
6. The process of claim 2 wherein the catalyst is ZSM-5 zeolite.
7. The method of claim 1 wherein the crystalline size of the zeolite is 0.01 to 20 $\mu$m.
8. The method of claim 1 wherein the crystalline size of the zeolite is 0.05 to 5 $\mu$m.

* * * * *